United States Patent [19]

Matzuk

[11] Patent Number: 4,479,388
[45] Date of Patent: Oct. 30, 1984

[54] ULTRASOUND TRANSDUCER AND DRIVE SYSTEM

[75] Inventor: Terrance Matzuk, Verona, Pa.

[73] Assignee: Dymax Corporation, Pittsburgh, Pa.

[21] Appl. No.: 420,473

[22] Filed: Sep. 20, 1982

[51] Int. Cl.³ .............................. G01N 29/00
[52] U.S. Cl. ........................ 73/634; 73/621; 73/633; 128/660; 310/268; 318/653
[58] Field of Search .............. 73/634, 614, 621, 633; 318/653, 685; 310/268; 128/660

[56] References Cited

U.S. PATENT DOCUMENTS

| | | | |
|---|---|---|---|
| 4,102,204 | 7/1978 | Kretz | 73/639 |
| 4,143,554 | 3/1979 | Nagy | 73/644 |
| 4,149,419 | 4/1979 | Cornell, Jr. | 73/639 |
| 4,187,455 | 2/1980 | Martin | 318/685 |
| 4,260,920 | 4/1981 | Nakamura et al. | 310/268 |
| 4,264,848 | 4/1981 | Jansen | 318/685 |
| 4,330,874 | 5/1982 | Sorwick | 73/620 |
| 4,349,770 | 9/1982 | Ragen | 318/653 |
| 4,366,422 | 12/1982 | Rhodes | 318/685 |
| 4,413,895 | 11/1983 | Lee | 310/268 |

Primary Examiner—Howard A. Birmiel
Attorney, Agent, or Firm—Weingarten, Schurgin, Gagnebin & Hayes

[57] ABSTRACT

An ultrasound probe includes an acoustical mirror that deflects an ultrasound beam generated by an ultrasound crystal toward an object under examination. The probe includes a thin flat motor whose rotor is controlled by a control system. The control system creates commutating signals that are applied to stator coils of the motor. An error signal that is related to the difference between the actual and desired positions of the object rotated by the motor is applied to the commutating signals to alter their amplitude or polarity to change the torque developed by the motor.

20 Claims, 16 Drawing Figures

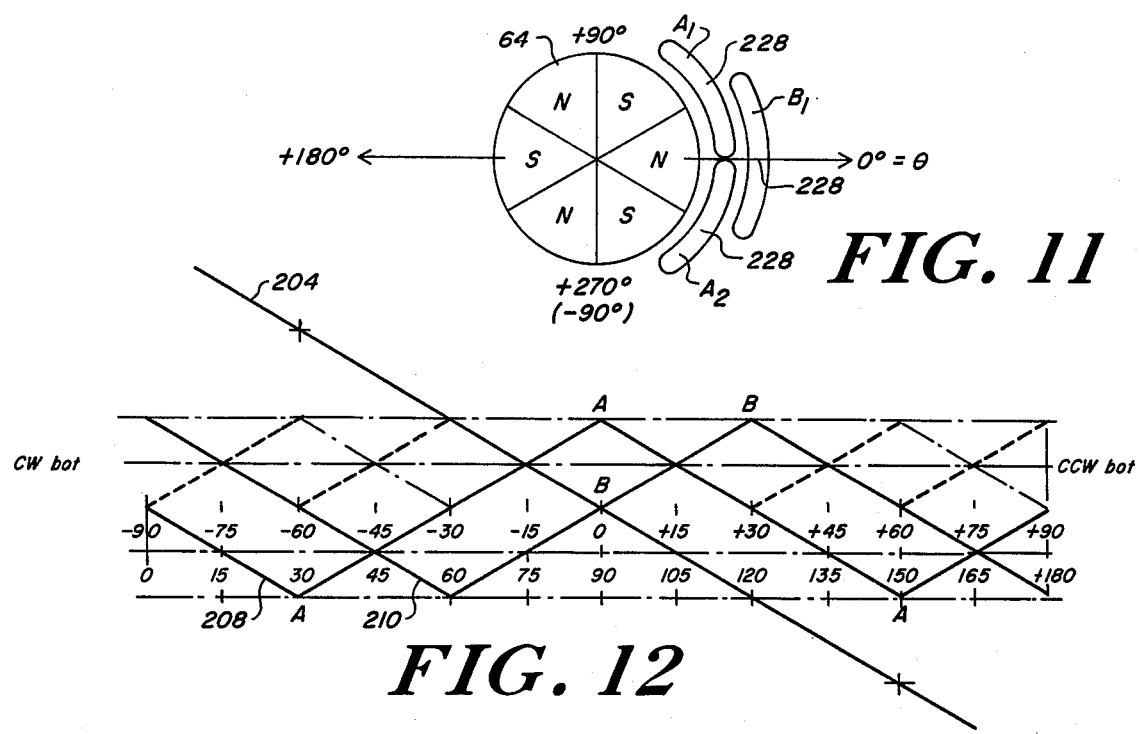
FIG. 11
FIG. 12
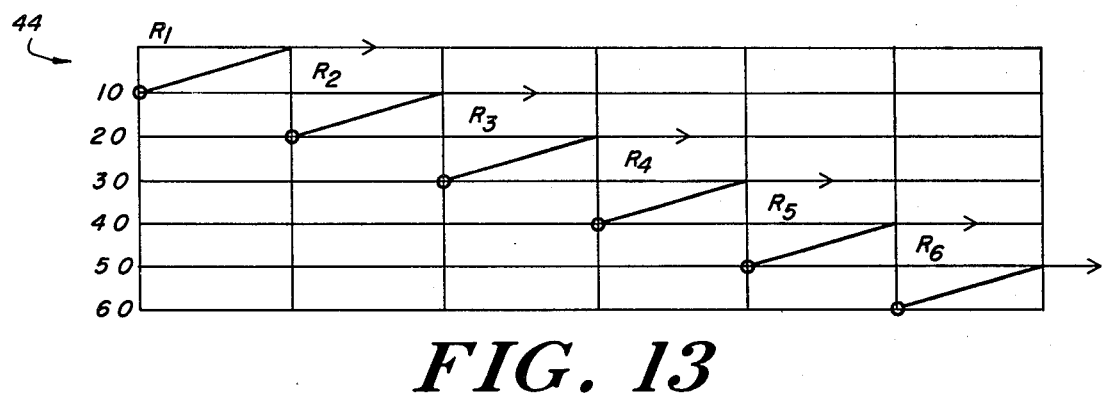
FIG. 13
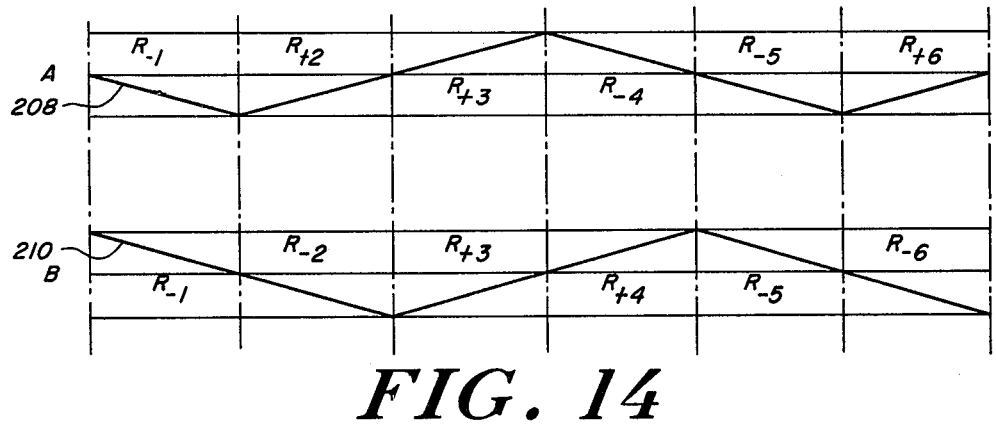
FIG. 14

ULTRASOUND TRANSDUCER AND DRIVE SYSTEM

BACKGROUND OF THE INVENTION

1. Field of the Invention

The present invention relates generally to apparatus employing ultrasound to examine an object and, more particularly, to an ultrasound probe and a drive system.

2. Description of the Prior Art

Physicians use apparatus commonly referred to as "ultrasonic scanning systems" to aid them during their examinations of patients. With an ultrasonic scanning system, a physician can obtain an image of a portion of a patient that is of interest. Further, ultrasonic scanning systems are used in a variety of nonmedical applications to obtain images of objects or portions of objects.

An important component of an ultrasonic scanning system is a piece of apparatus commonly referred to as an "ultrasound transducer probe", an "ultrasound probe" or, simply, a "probe". The ultrasound probe is used to direct into the patient a timed series of pulses of ultrasound energy ("incident beam") and to receive and convert to electrical signals the series of ultrasound echoes reflected from acoustical interfaces located within the patient ("echo beam"). The nature of the ultrasound echoes and the nature of the electrical signals derived from those echoes are indicative of the nature of the acoustical interfaces which reflected them. Accordingly, proper processing of electrical signals derived from an echo beam yields a display that shows a point of each acoustical interface encountered by the incident beam. Similarly, a number of incident beams directed through a section of the patient produces a corresponding number of returning echo beams which can be processed to create an image of that section of the patient.

One type of ultrasound probe (referred to hereinafter as a "moving crystal probe") employs a single moving ultrasound crystal (the element that creates the pulses of ultrasound energy), several moving crystals, or a single moving crystal having several electrically distinct beam-producing regions (also known as an annular array crystal). Such a probe must have apparatus for moving the crystal to cause it to direct a series of incident beams through a section of the patient. Most ultrasound probes designed to date use a conventional electric motor that oscillates or rotates a crystal to cause the probe to scan a sector of the patient. One probe, which is disclosed in U.S. Pat. No. 4,092,867, has a crystal mounted directly to a magnet that is mounted for rotation between two legs of an electromagnet. The direction of the current applied to the electromagnet is periodically reversed to cause the magnet and crystal to oscillate and permit the crystal to scan a sector of a patient. Another type of ultrasound probe (referred to hereinafter as a "moving mirror probe") employs an acoustical mirror and one or more stationary crystals. The acoustical mirror is moved to cause the incident beams generated by the stationary crystal to be scattered through a sector of the patient under examination. Moving mirror probes are preferrable to moving crystal probes under certain well-known conditions for example, when the probe is designed to employ an annular array crystal. Generally, a moving mirror probe eliminates the problems associated with commutating to a moving crystal—and, in particular, an annular array crystal—electrical energy needed by the crystal to generate ultrasound pulses and to commutate from the crystal electrical signals created from echoes received by the crystal. Again, conventional electric motors are usually used to move the acoustical mirror.

Two problems are associated directly with the use of conventional electric motors in ultrasound probes. First, the motion of the motor must be transferred to the mirror or crystal by some sort of mechanical linkage. Such a transfer of motion does not permit the precise position control of the mirror or crystal that is required to produce high quality ultrasound images. Also, the linkage causes mechanical vibrations that cause the probe to vibrate and further introduces errors into the information transferred by the probe to the video equipment of the scanning system—both of which adversely affect image quality by misregistering the locations of image features.

Control of mirror or crystal motion is accomplished generally—if at all—with electrical control of motor motion. Conventional electric motors and control schemes, however, have not provided a completely satisfactory solution to the problem of precise motion control of acoustical mirrors and crystals. Many stepping motors are capable of stopping only at a number of angular increments equal to the number of wound poles or equal to a small multiple of the number of poles. Commonly, digitally controlled stepping motors are capable of stopping at 200 positions per revolution, or at 360/200 degrees per increment. However, extremely precise motion control and stopping ability—which are required of ultrasound probe motors to enable probes to produce high quality images—would require an impractically large number of coils. Further, a stepping motor having a large number of poles would have limited angular velocity due to the limitations imposed by the required switching frequency. Moreover, the rotor of a stepping motor cannot be made to accelerate and decelerate frequently at approximately 2,000 radians/-second$^2$ (the level of acceleration and deceleration that an ultrasound probe motor must achieve) without risking damaging the motor because the stepping motor must carry a high inertia permanent magnet energy field.

DC motors having small low inertia printed circuit rotors have been used in the types of control systems employing an optical shaft encoder. However, such motors have two sided field magnet assemblies that are physically large and, accordingly, do not provide the performance that an ultrasound probe motor must provide to permit the probe to produce a high quality image. Further, such motors must be sealed from such harmful working environments as the ultrasound transmissible liquid of an ultrasound probe to avoid interaction of the commutation contacts of the motor with the environment. For example, any conventional DC motor in a servo control loop must be isolated from corrosive or combustible liquids or gases to avoid combustion or damage to the commutating devices within the motor. Many conventional low inertia DC motors that are used with electronic commutation designs provide indirect access from the rotor to the load due to intervening bearings or overhanging magnet assemblies.

Accordingly, there exists a need for an ultrasound probe having a moving acoustical mirror, the position of which can be controlled precisely at all times. Further, there exists a need for a drive system which can be used to move an ultrasound crystal or acoustical mirror of a probe in a precise manner. In particular, there exists a need for an ultrasound probe drive system which provides rapid positioning and accurate stopping of a crystal or mirror. Ideally, the drive system should be able to stop a rotating mirror or crystal at a position that is less than 0.1 degree from a commanded position and should be able to accelerate at greater than ±2,000 radians/second$^2$. The drive system should permit access to the mirror or crystal and there should be minimum overhang of motor electromagnets, field magnets, or commutation devices. Preferably, the bearing system of the drive system should be lubricated directly by the hostile fluid environment in which the drive system is immersed.

SUMMARY OF THE INVENTION

The present invention provides an ultrasound transducer that includes a sealed housing that contains an ultrasound energy transmissible liquid and apparatus disposed within the housing for emitting ultrasound energy and converting the ultrasound energy to electrical signals. The apparatus is movably mounted within the housing for deflecting the emitted ultrasound energy and for deflecting returning ultrasound energy to the receiving apparatus. The ultrasound probe incorporates the driving system of the present invention which drives an object that is movable relative to the stator assembly of its driving motor. The stator assembly is thin and flat and has at least two sets of electrically conductive coils, at least one coil set being displaced from at least one other coil set. The driving motor includes a thin flat permanent magnet assembly mounted in confronting relationship to the stator assembly and being movable relative thereto. The magnet assembly has a plurality of magnetic poles. The drive system includes apparatus for providing a position signal related to the position of the object relative to the stator assembly. Apparatus is provided for processing the position signal to generate commutating signals in a number corresponding to the number of coil sets. Apparatus is provided for generating a command signal and for comparing the position signal with the command signal and thereby generating an error signal. Apparatus is provided for applying the error signal to the commutating signals to alter at least one of their amplitude and polarity. Finally, the drive system includes means for applying the commutating signals as current commands to their respective coil sets.

It should be noted that the ultrasound probe of the present invention can be used in medical and nonmedical applications. Further, the drive system of the present invention can cause an object to move in a variety of paths, including rotating and linear paths.

BRIEF DESCRIPTION OF THE DRAWINGS

The following detailed description of the preferred embodiments can be understood better if reference is made to the accompanying drawings in which:

FIG. 11 is a schematic view of a portion of the probe in FIG. 1 illustrating the magnet assembly and several stator coils;

FIG. 12 is a graph that shows plots of the actual position of the signal and the current applied to the sets of stator coils;

FIG. 13 is a plot showing the ramp functions which can be combined with each other to produce the signals applied to the stator coils;

FIG. 14 is a plot showing the manner in which the ramp functions illustrated in FIG. 13 are combined to construct the signals applied to the stator coils;

DETAILED DESCRIPTION OF THE PREFERRED EMBODIMENTS

Figure 1:
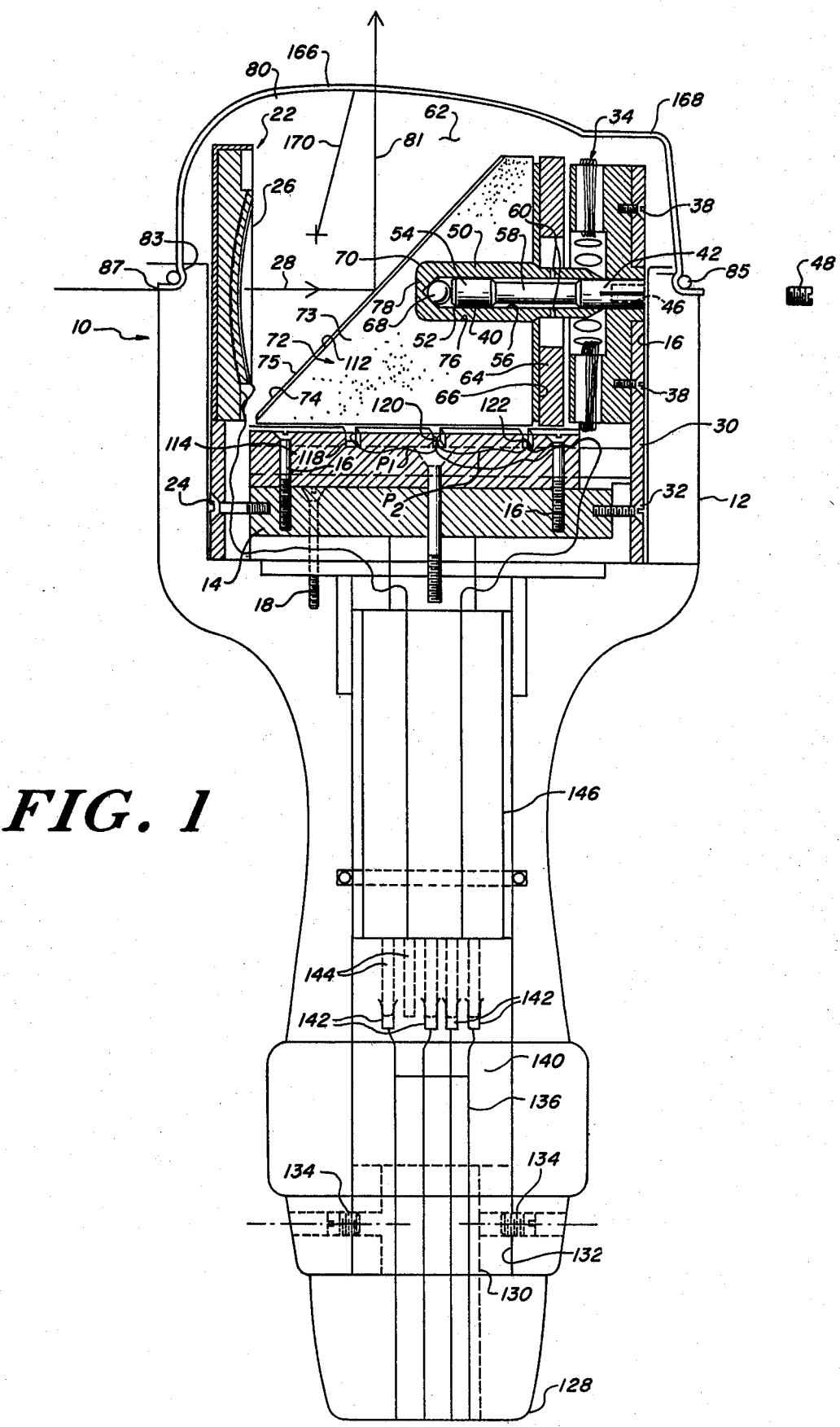
FIG. 1 is a sectional view of an ultrasound probe constructed according to the provisions of the present invention.

FIGS. 1 through 7 and 16 illustrate the mechanical components of the preferred embodiment of the present invention. The mechanical components of ultrasound probe 10 are housed within a case 12 which is molded from industrial electronic grade epoxy. A cavity 16 is formed in the upper portion of case 12 and receives the ultrasound crystal, acoustical mirror, and drive system of probe 10. A mounting block 14 is secured to the bottom of cavity 16 with a pair of screws 18. An ultrasound crystal assembly 22 is secured to one end of mounting block 14 with a pair of screws 24. Ultrasound crystal 26 of ultrasound crystal assembly 22 emits ultrasound pulses along line 28 of FIG. 1.

Motor mounting 30 is secured to the remaining end of mounting block 14 with a pair of screws 32. Stator assembly 34, which includes stator coils A and B, of motor 36 is secured to motor mounting 30 with a pair of screws 38. One end 42 of a pinion 40 is secured within a opening 106 formed in stator assembly 34. End 42 of pinion 40 is split and defines an opening 46 adapted to receive a threaded set screw 48. The outer diameter of set screw 48 is slightly larger than opening 46. Accordingly, threading set screw 48 within opening 46 causes end 42 of pinion 40 to expand and bear against stator assembly opening 44 to secure end 42 of pinion 40 to stator assembly 34. Mirror mounting 50 defines a passage 52 which receives a portion of pinion 40. Enlarged ends 42 and 54 of pinion 40 bear against wall 56 of passage 52. Shaft 58 has a smaller diameter than ends 42 and 54 of pinion 40 to provide space between shaft 58 and wall 56 of passage 52. One end of mirror mounting 50 defines a pair of openings 60 which permits acoustical liquid 62 (liquid which transmits ultrasound energy) disposed within cavity 16 to flow within passage 52 and lubricate pinion 40 as mirror mounting 50 rotates around it.

A rotor or magnet assembly 64 is secured with epoxy to surface 66 of mirror mounting 50. A ball bearing 68 is located in passage 52 between end 54 of pinion 40 and end wall 70 of passage 52 to reduce friction as mirror mounting 50 rotates around pinion 40. An acoustical mirror assembly 72 includes a mirror suport 73, mirror 75 and an acoustical reflective surface 74. Support 73 defines a passage 76 which receives protrusion 78 of mirror mounting 50.

Ultrasound crystal 26 can be any desired type of ultrasound crystal. For purposes of describing the preferred embodiment, crystal 26 shall be a single crystal having one pulse generating region. Crystal 26 emits ultrasound pulses along line 28 toward reflective surface 74 of acoustical mirror assembly 72. The pulses strike surface 74 which reflects them through cover 80 generally along axis 81. When stator assembly 34 is energized by a suitable source of electrical energy, rotor assembly 64 is rotated in a predetermined fashion, which causes mirror mounting 50 and mirror assembly 72 to rotate about pinion 40. The rotation of mirror assembly 72 causes incident beams of ultrasound pulses emitted by crystal 26 to be directed through a section of an object toward which the probe 10 is aimed. In the preferred embodiment, the electronic system, described in detail below, causes mirror assembly 72 to oscillate between two limits and direct incident beams emitted by crystal 26 through a sector defined by those limits.

FIGS. 1, 3, 7 and 16 show ultrasound crystal assembly 22 and the manner in which it is mounted in probe 10. Crystal assembly 22 includes crystal mounting 82 which is secured to one end of mounting block 14 with screws 24. Crystal mounting 82 includes circular cavity 84 which is adapted to receive a plate 86. Wall 88 of cavity 84 defines an opening that is slightly smaller at its outermost edge than the diameter of plate 86. Accordingly plate 86 can be snapped into cavity 84 and held therein by wall 88. Ultrasound crystal 26 is secured to surface 90 of plate 86 with a suitable epoxy. Two electrical connections 92 provide electrical communication with crystal 26 and leave crystal assembly 22 along channel 94 formed in the base of crystal mounting 82.

Stator assembly 34 is shown in FIGS. 1, 2, 3 and 6. Stator assembly 34 includes a core 96 upon which coils A and B of stator assembly 34 are wound. Core 96 can be constructed from leaded steel and should be coated with baked epoxy. A series of twelve holes 98 are machined through the wall of core 96. A corresponding series of slots 100 are formed in surface 102 of core 96. Slots 100 permit the wires which form stator coils A and B to be placed within holes 98. The projected longitudinal axis of each slot 100 and each hole 98 is offset from the center of core 96 by 0.09 inches. That offset prevents alignment of the coils of stator assembly 34 and the magnetic poles of rotor assembly 64, which alignment would cause rotor assembly 64 to cog as it is rotated by stator assembly 34. Two coils A and B, having six windings each, are wound on core 96 through holes 98. Each coil A and B is displaced angularly from the other by thirty mechanical degrees. Accordingly, the wire comprising a set of coils A and B passes though every other hole 98 of core 96. Each winding of a set of coils A and B is wound opposite to that of adjacent windings of that set. Accordingly, when coil A or B is energized, the polarity of the magnetic field generated by a winding is opposite to that of each adjacent magnetic field created by each adjacent winding of that set. Therefore, there are four electrical connections leaving stator assembly 34. Stator assembly 34 includes a pair of holes 104 through which a pair of screws 38 are threaded to secure stator assembly 34 to motor mounting 30. As described above, end 42 of pinion 40 is secured within opening 106 of core 96 with a set screw 48.

FIGS. 1, 2, 3 and 5 show permanent magnet assembly or rotor assembly 64. Magnet assembly 64 consists of three magnet segments 108 having a north magnetic pole facing stator assembly 34 and three magnet segments 110 having a south magnetic pole facing stator assembly 34. Each segment 108 or 110 is machined from a soft machinable magnetic material and is secured to adjacent segments with a suitable epoxy. Segments 108 and 110 are so secured together that each segment 108 or 110 is located between segments having a polarity opposite to its polarity. As described above, permanent magnet assembly 64 is secured to surface 66 of mirror mounting 50 with epoxy. Stops 111 are secured to the edge of two magnet segments and contact position mounting block 114 to prevent over-rotation of rotor assembly 64.

Figure 2:
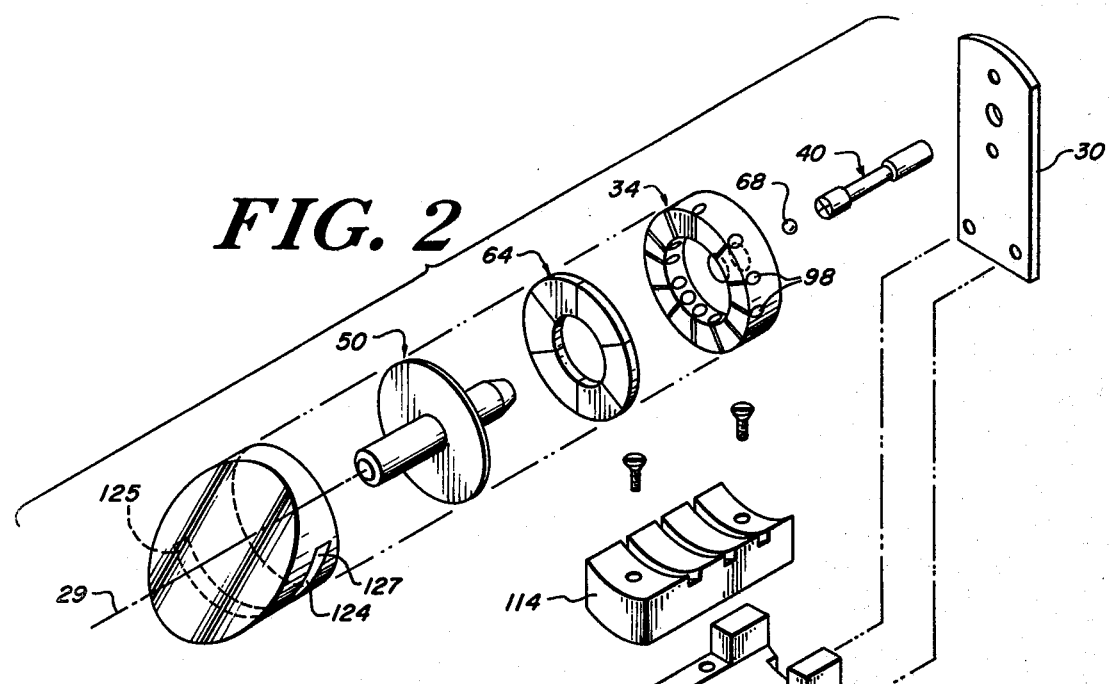
FIG. 2 is an exploded view showing the acoustical mirror, the physical components of the motor and the mounting block of the probe shown in FIG. 1.
Figure 16:
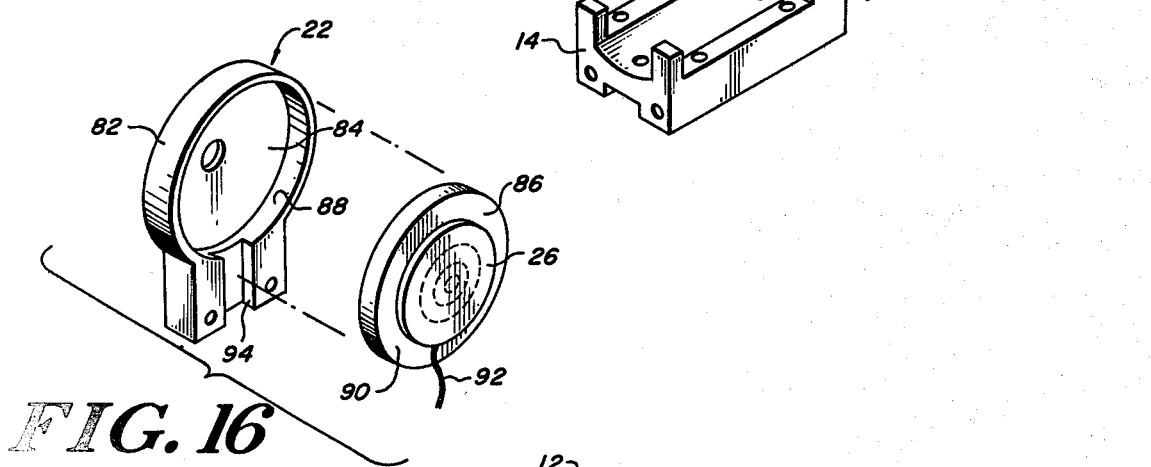
FIG. 16 shows the ultrasound crystal assembly of the probe shown in FIG. 1.
Figure 3:
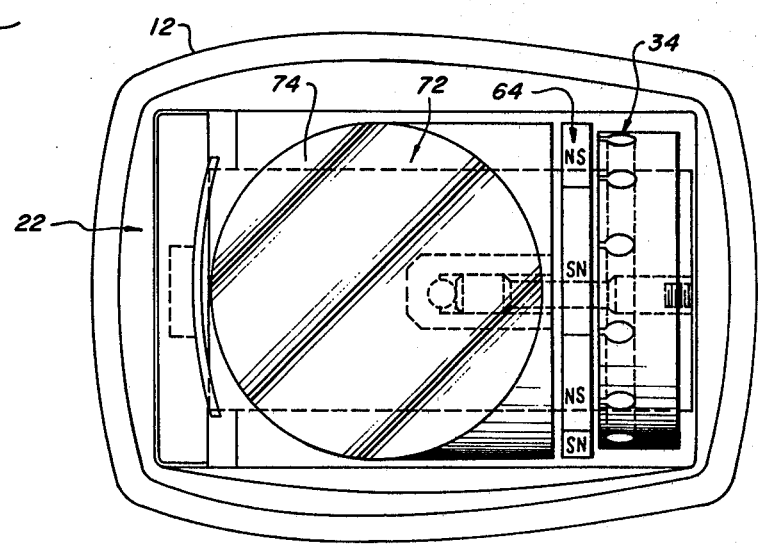
FIG. 3 is a sectional view of the probe shown in FIG. 1 taken along the line III—III.
Figure 4:
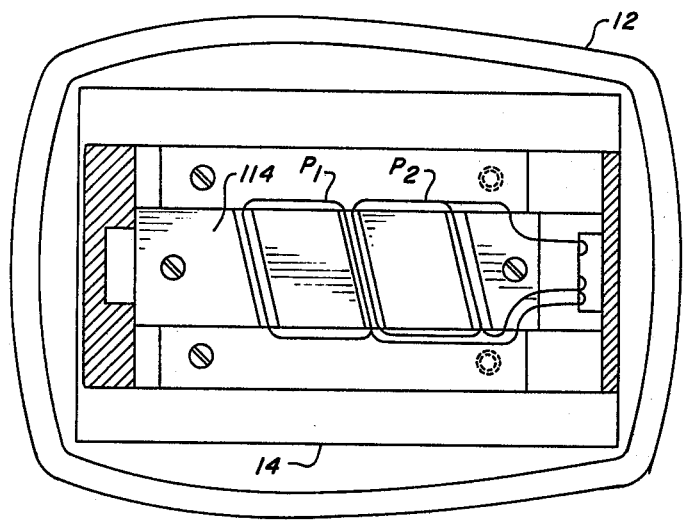
FIG. 4 is a sectional view of the probe shown in FIG. 1 taken along the line IV—IV.

FIGS. 1, 2 and 3 show acoustical mirror assembly 72. Mirror assembly 72 is secured to surface 112 of mirror mounting 50 with epoxy. Mirror support 73 is molded from an isocyanate similar to styrofoam. Mirror support 73 has an outer surface without pores. Mirror surface 74 of mirror 75 is suitably bonded to mirror support 73.

The general configuration of mirror 75 and the support 73 comprises an ellipse mounted in an inclined position on a cylindrical barrel. The complement of this configuration is fashioned out of a teflon rod that slips into a teflon tube constructed of the same material as is the rod, thereby forming a plastic molding form. One method of fabricating mirror assembly 72 consists of mixing isocyanate foam with a catalyst and pouring the mixture into the molding form, and allowing the foaming mixture to expand upwards beyond the open end of the mold. The lower surface of the molded foam, being formed against the elliptical surface, is free of pores, and comprises an excellent acoustical reflector. The upper end of the molded part is cut transverse to the correct length, and a hole is drilled part way into the cut surface to accept protrusion 78.

An alternate method is to mold the rod out of a low melting temperature metallic alloy and to electroplate the elliptical end with copper or nickel. The electroplated surface is chemically etched and inserted into the tubing. The isocyanate foam cylinder is molded against the electroplated surface and the alloy rod is melted in warm water. This type of mirror assembly 72 has the advantage of having greater immunity to absorption of the working liquid 62 of probe 10.

Magnet assembly 64 exerts a strong attractive force on stator assembly 34 which holds it, mirror mounting 50, and mirror assembly 72 in place on pinion 40 during normal use of probe 10. The force exerted by rotor 64 on stator assembly 34 is the only means employed to keep those components in place on pinion 40.

A position coil mounting block 114 is secured to mounting block 14 with a pair of screws 116. Block 114 is machined from cast acrylic and defines three slots 118, 120 and 122 which are adapted to receive the electrical wires comprising the position sensing coils P1 and P2 of probe 10. A first coil P1 is formed by winding forty-two turns of electrical wire through slots 118 and 120 and a second coil P2 is formed by winding forty-one turns of electrical wire through slots 120 and 122. The direction in which each coil P1 and P2 is wound is opposite to that in which the remaining coil is wound. Only the final return wires of the coils P1 and P2 are joined together (see FIG. 8). Accordingly, three electrical connections—two active leads and one return lead—are connected to block 114. As shown in FIG. 2, a position sensor strip 124, which is a generally rectangular piece of aluminum approximately 0.002 inches thick, is bent to conform to the outer surface of mirror support 73 and is so secured thereto that strip 124 assumes an axially spiralling shape. That is, one end 125 of strip 124 is secured to mirror support 73 at a point that is farther from rear surface 126 than the point at which the remaining end 127 of sensor strip 124 is secured to support 73. Each coil P1 and P2 of block 114 emits an alternating magnetic field when it is energized by a suitable source of high frequency alternating electric current. As mirror assembly 72 rotates, sensor strip 124 passes through the magnetic flux established by energized coils P1 and P2. When a portion of strip 124 is in a magnetic field established by a coil P1 or P2, that portion of strip 124 partially cuts off the magnetic flux emanating from that coil and reduces the inductance of the coil. Since strip 124 is secured to mirror support 73 in a position that makes it skewed with respect to axis 79 of generally cylindrically shaped mirror support 73, the extent of the portion of strip 124 that interferes with the magnetic field emanating from a coil P1 or P2 depends on the angular position of mirror assembly 72 with respect to block 114. Accordingly, the inductance of a coil P1 or P2 and, accordingly, the voltage established across the coil, depends on the angular position of mirror assembly 72 with respect to block 114. An electrical position signal can be derived from the voltage appearing across coils P1 and P2 the level of which is dependent on the angular position of mirror 72 and provides an indication of the position of mirror 72. The nature of the position signal (bearing reference numeral 204) derived from coils P1 and P2 and the use to which that signal is put is described in detail below. It should be noted that although one coil could be used to generate a position signal, two coils are used to cancel errors in the signal created by sources of interference. The two signals derived from coils P1 and P2 are subtracted from each other thereby suppressing errors while adding position information contributed by coils P1 and P2. Therefore, it can be seen that when the difference between the level of the coil voltages is large, mirror assembly 72 is at one of its limits of oscillation; when that difference is small, mirror assembly 72 is somewhere near the middle of its oscillation. In any event, subtraction of the two signals nullifies any errors in those signals.

Figure 5:
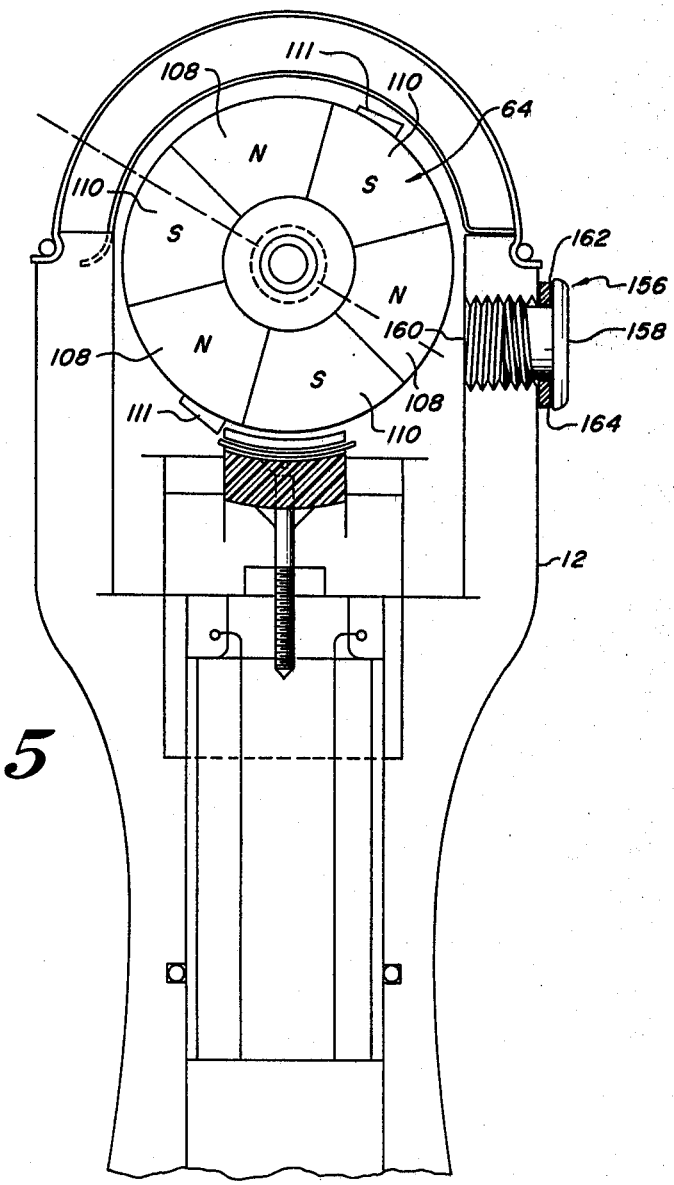
FIG. 5 is a sectional view of the probe shown in FIG. 1 taken along the line V—V.
Figure 6:
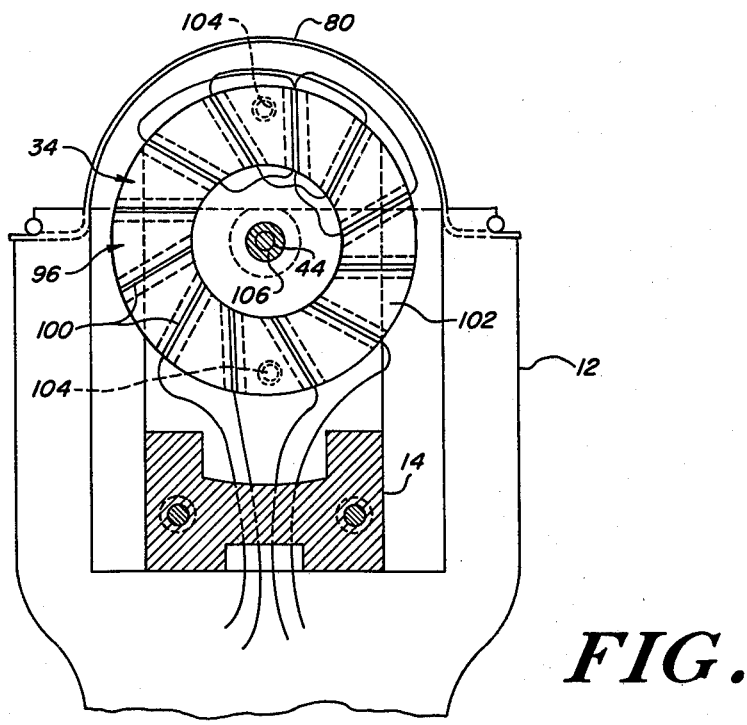
FIG. 6 is a sectional view of the probe shown in FIG. 1 taken along the line VI—VI.
Figure 7:
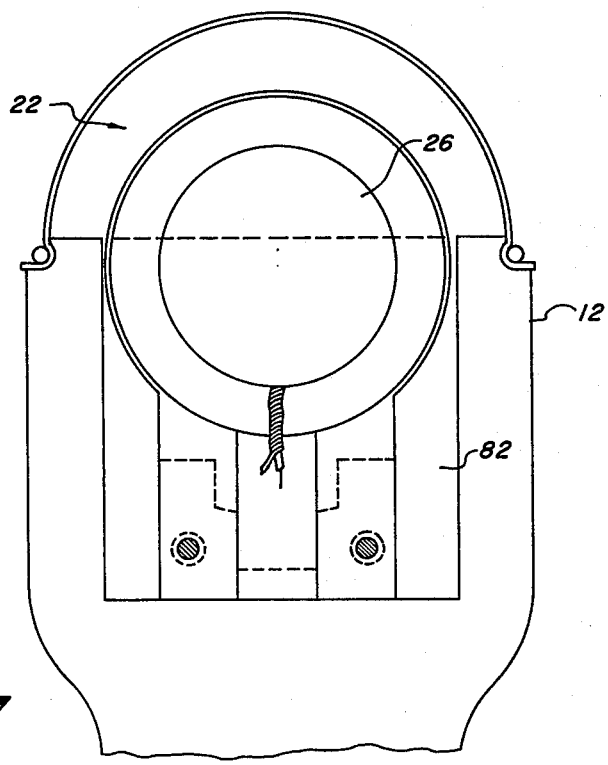
FIG. 7 is a sectional view of the probe shown in FIG. 1 taken along the line VII—VII.

FIGS. 1 and 5 show the manner in which electrical communication between the electrical components of probe 10 and the remainder of the ultrasound scanning system is achieved. If crystal 26 is not an annular array crystal and, accordingly, requires only two electrical connections, nine electrical leads must be brought from within case 12 and must communicate electrically with the ultrasound scanning system—four leads from motor 36, two leads from crystal 26, and three leads from position sensing block 114. Those nine leads exit probe 10 by way of a cable 128. A sleeve 130 is secured within a passage 132 formed in the lower portion of case 12 with a pair of set screws 134. End 136 of cable 128 is potted in a socket 140. Nine female spring contacts 142 are potted within socket 140 and are adapted to receive nine corresponding prongs 144 secured to the bottom of brass plug 146. The nine leads exiting cavity 16 terminate at prongs 144. An O-ring 145 is disposed within annular channel 148 and prevents liquid 62 from passing between the wall of passage 132 and plug 146. An epoxy fitting 150 is secured with an epoxy glue to the top surface of plug 146 and secured to the bottom of mounting 14 with a screw 152. The electrical leads of crystal 26, block 114 and stator coils A and B pass through fitting 150 from cavity 16 and into brass plug 146.

The upper portion of case 12 defines an opening 154 adapted to receive a threaded plug 156 constructed from clear acrylic. Surfaces 158 and 160 are polished to permit visual inspection of the interior of cavity 16 through those surfaces. Plug 156 defines a flange 162 into which an O-ring 164 is secured. O-ring 164 should be no harder than 35 durometers to permit tightening of filler plug 156 by hand. Because plug 156 is clear, bubbles within acoustical liquid 62 that would adversely affect image quality can be detected and eliminated. Further, the transparency of plug 156 permits visual detection of movement of mirror assembly 72 and centering of mirror assembly 72 when the control system of probe 10 is calibrated.

FIGS. 1, 5, 6, 7 and 17 show cover 80 of probe 10. Cover 80 includes a large portion 166 and a smaller portion 168. Cover 80 is secured in place on case 12 by placing flanged edge 87 of cover 80 within flange 83 of case 12. A band 85 is stretched around cover 80 and placed around flanged edge 87 to secure cover 80 in place. When cover 80 is in place on top of case 12, small portion 168 generally encloses motor 36 and larger portion 166 encloses crystal assembly 22 and mirror assembly 72. The incident beams generated by crystal 26 pass through larger portion 166 of cover 80. The radius 170 of larger portion 166 is 2.3 inches. It is important to so form larger portion 166 of cover 80 that it is noncylindrical to ensure that there is minimal and off-axis distortion of the incident beams as they pass through cover 80. Also, it is important to so form cover 80 that the thickness of portion 166 is equal to one-half of the acoustical wavelength at the acoustical frequency of crystal 26 to minimize the reflection of incident beam from the interior surface of portion 166 to crystal 26.

Figure 8:
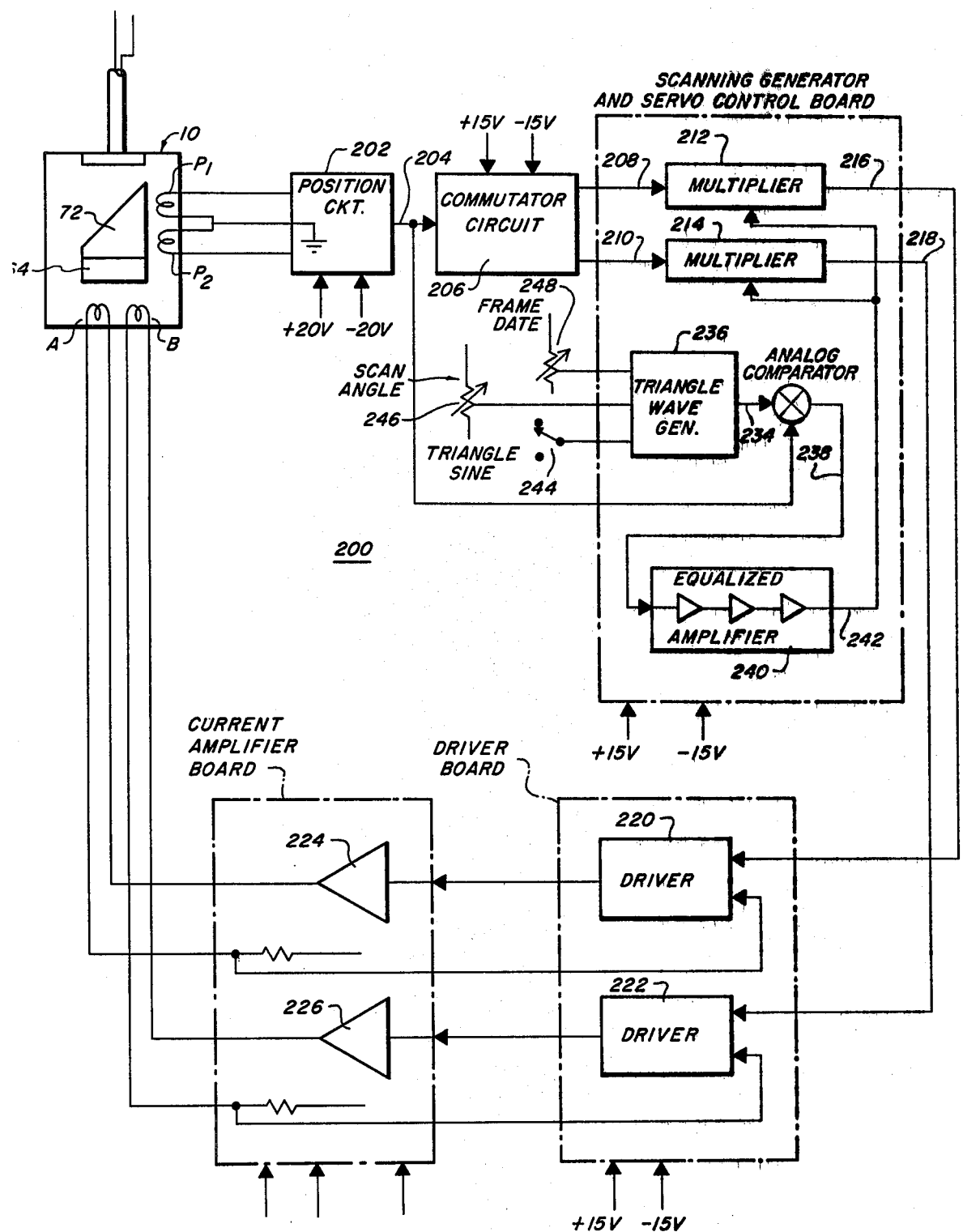
FIG. 8 is an illustration in block diagram form showing the motor drive and control system for the probe shown in FIG. 1.

FIG. 8 shows generally, in block diagram form, the control system 200 used to control the position of mirror assembly 72. In the preferred embodiment control system 200 oscillates mirror assembly 72 between two limits; however, control system 200 can be commanded to move mirror assembly 72 in any direction or combination of directions, or at any speed or combination of speeds, or any combination of directions and speeds. The components shown in FIG. 8 that are illustrated outside transducer block 10 are located in cabinetry which houses the remaining components of the ultrasound scanning system. System 200 applies to coils A and B a pair of triangular energizing signals 209 and 211 that are offset angularly from each other by thirty degrees and that have an amplitude and polarity that depend on the difference between the actual and desired positions of mirror assembly 72. Generally, the greater the amplitude of signals 209 and 211, the greater the torque that is experienced by rotor assembly 64.

Probe 10 is shown schematically in FIG. 8 as a block that contains mirror assembly 72, rotor assembly 64, stator coils A and B and position sensing coils P1 and P2. As described above, rotation of mirror assembly 72 changes the inductance of and the voltage developed across coils P1 and P2. In the preferred embodiment of the present invention, control system 200 commands mirror assembly 72 to oscillate between two limits at a precisely controlled angular velocity. Accordingly, position circuit 202 creates from the voltage developed across coils P1 and P2 the position signal 204 shown in FIG. 12. It should be noted that signal 204 is linear with respect to the angular displacement of mirror assembly 72 as is shown in FIG. 12. Position signal 204 is used for two purposes. It enables control system 200 to correct any error in the position of mirror assembly 72, as is described in detail below. Also, position signal 204 is used by commutator circuit 206 to create commutating signals 208 and 210. Commutating signals 208 and 210 are triangular waves versus angle which are offset angularly from each other by thirty degrees. Multipliers 212 and 214 establish the polarity and alter the amplitude of signals 208 and 210 in a manner that depends on the difference between the actual and desired position of mirror assembly 72. The altered energizing signals 216 and 218 are fed to driver circuits 220 and 222. Driver circuits 220 and 222 compare the voltages at their inputs to the voltages obtained by current sampling resistors 225 and 227 of current amplifiers 224 and 226 to ensure that the currents flowing in stator coils A and B are directly proportional to the voltage output of multipliers 212 and 214, thereby establishing the commanded torque on rotor assembly 64. Current amplifiers 224 and 226 boost the voltage at the output of drives 220 and 222 to a current level that enables coils A and B to produce the commanded torque.

FIGS. 11 through 14 illustrate the manner in which stator assembly 34 is energized. FIG. 11 is a schematic view of rotor assembly 64, a pair of adjacent windings—A1 and A2—of coil A and a winding B1 of coil B. FIG. 12 is a graph showing position signal 204 and commutator signals 208, and 210. FIG. 13 shows the timed ramp functions which are used to construct signals 208 and 210. FIG. 14 shows the manner in which the signals shown in FIG. 13 are combined to produce signals 208 and 210. When windings A1 and A2 are energized, the magnetic poles of the fields created by those windings can be considered to exist at points 228. Accordingly, north magnet segment 230 experiences maximum torque due to winding A1 and A2 at theta equal to zero. It experiences no torque at theta equal to plus or minus thirty degrees. Accordingly, the windings of coil B are displaced spacially from those of coil A by thirty degrees to ensure that rotor assembly 64 experiences torque even when its magnet segments are experiencing no torque due to one of the coils. To ensure that rotor assembly 64 experiences continuous and uniform torque in one direction from a coil (when desired) the direction of current flow in each winding of that coil must be reversed every sixty degrees of rotation of rotor assembly 64. Accordingly, as shown in FIG. 12, the commutating signals 208 and 210 and the energizing signals 209 and 211 are triangular waves which pass through the zero axis every sixty degrees. Also, each signal of a set is offset from the other signal of the set angularly by thirty degrees.

FIG. 13 shows the ramp functions that are used to construct commutating signals 208 and 210. Each ramp function R1 through R6 begins at zero volts and increases linearly with angle until it reaches plus five volts, at which level it is clamped and remains constant. The ramps R1 through R6 begin at thirty degree intervals; accordingly, each ramp RN begins at an angle that is offset by thirty degrees from the ramps RN−1 and RN+1 created before and after it. FIG. 14 illustrates the combination of ramps R1 through R6 needed to produce each commutating signal 208 and 210.

The torque applied to mirror assembly 72 is changed if there exists an error between the desired and actual positions of mirror assembly 72 by changing the amount of current flowing through coils A and B. To determine whether such a correction is necessary, position signal 204 is fed to analog comparator 232, where it is subtracted from scanning wave 234 created by scanning wave generator 236. In the preferred embodiment, scanning wave generator 236 generates either a triangular or sinusoidal scanning wave 234, depending on the setting of switch 244. The difference between signals 204 and 234 is the error signal 238 which is fed to equalized amplifier 240. Equalized amplifier 240, which includes two differentiators, suitably amplifies and accentuates rapid changes in error signal 238 and applies the amplified and accentuated error signal 238, as signal 242, to multipliers 212 and 214. Depending on the sign of signal 242, multipliers 212 and 214 multiply signals 208 and 210 by either a positive or a negative value. Switch 244 permits the scanning signal 234 to be changed from a triangular wave to a sine wave, which change would cause mirror assembly 72 to move more slowly at the limits of its oscillation. Potentiometer 246 permits modification of the limits of oscillation. Potentiometer 248 permits modification of the rate at which the frames of the image are displayed.

Figure 9:
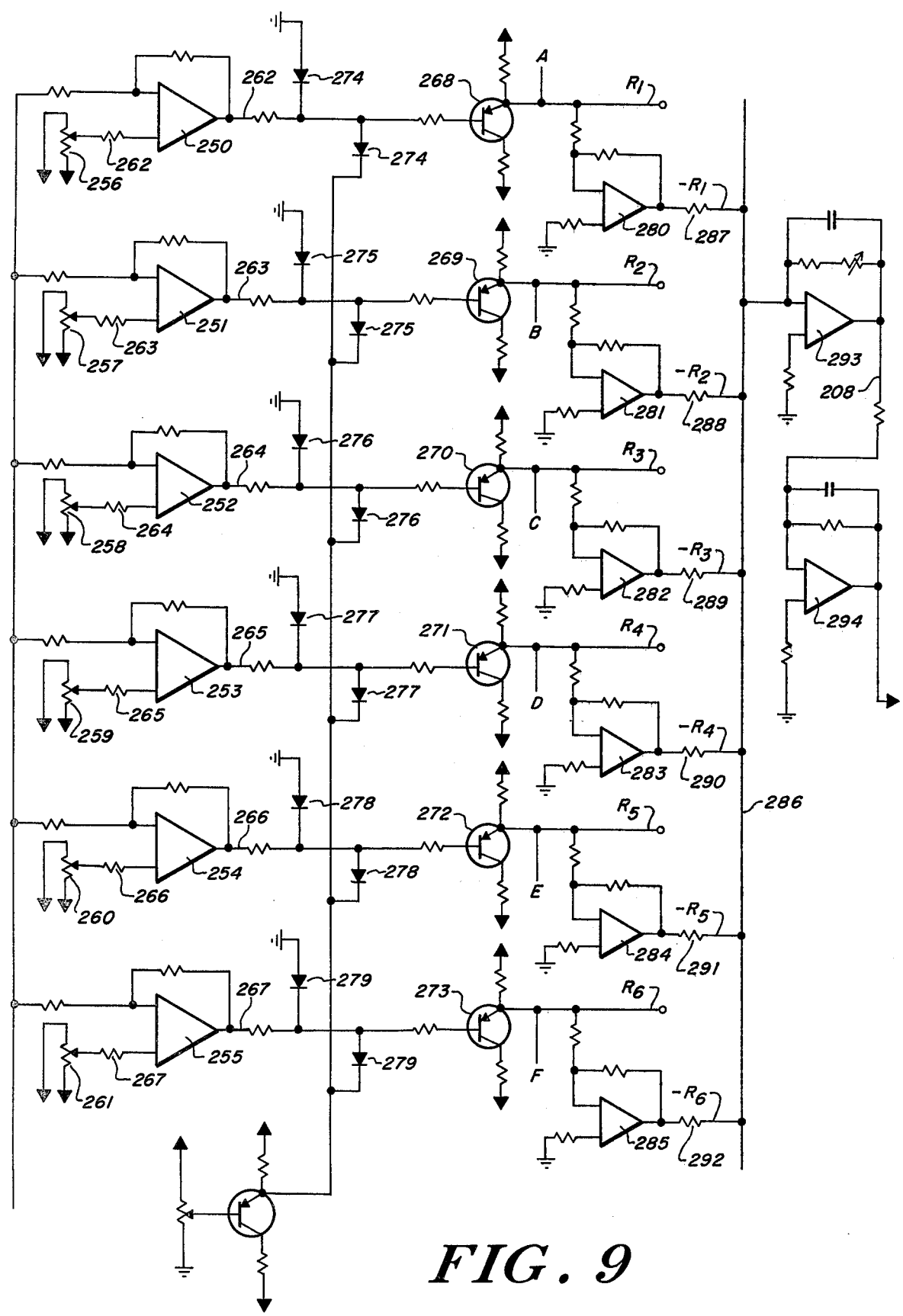
FIGS. 9 and 10 are schematic circuit diagrams illustrating the commutator circuit for the probes shown in FIG. 1.
Figure 10:
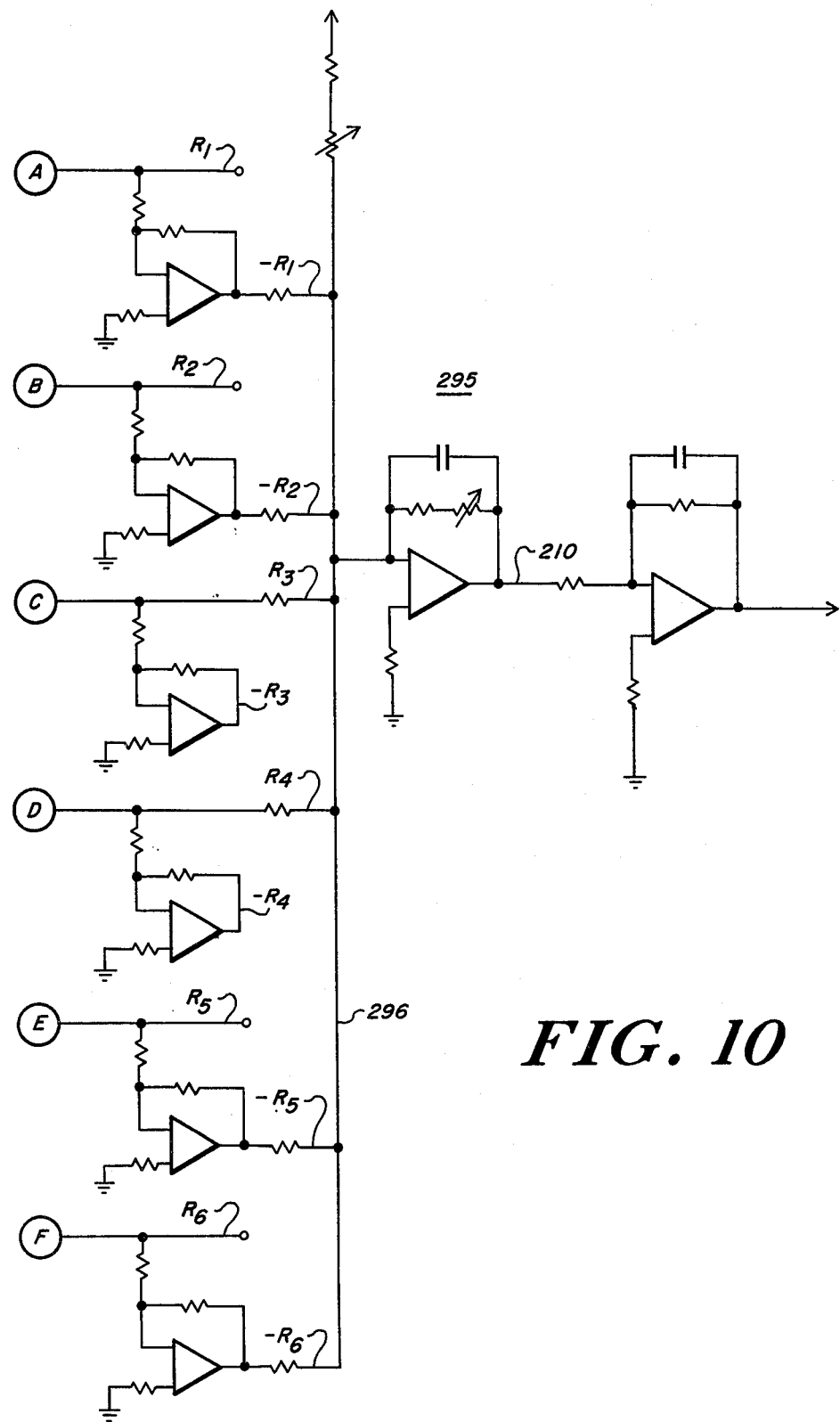
Figure 15:
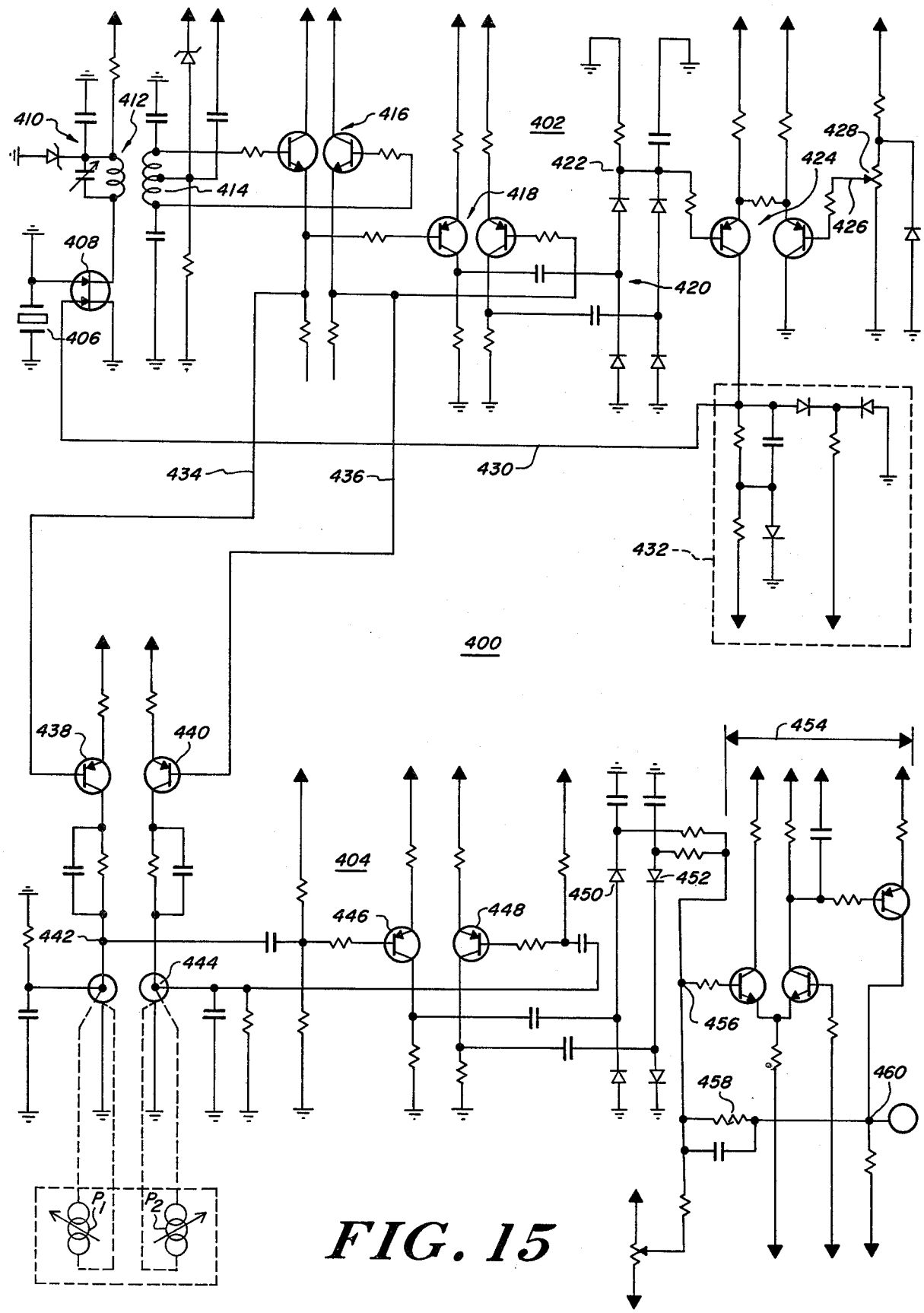
FIG. 15 is a circuit diagram showing the position sensor circuit for the probe shown in FIG. 1.

FIGS. 9, 10 and 15 illustrate the commutation and position sensor circuits. The remainder of the circuits shown in FIG. 8 are conventional. FIG. 9 illustrates the circuit that creates commutating signal 208. Position signal 204 is applied to operational amplifiers 250 through 255. By suitably adjusting potentiometers 256 through 261, a range of voltages is caused to appear across resistors 262 through 267, respectively, which causes operational amplifiers 250 through 255 to begin creating ramp functions R1 through R6 at thirty degree intervals, as shown in FIG. 13. The outputs of amplifiers 250 through 255 are the ramp functions 262 through 267, which correspond generally to ramp functions R1 through R6 shown in FIG. 13. Ramp functions 262 through 267 are amplified by line drivers 268 through 273 and are clamped between the levels of zero and five volts by diode pairs 274 through 279. The outputs of line drivers 268 through 273, R1 through R6, respectively, are inverted by inverters 280 through 285 to produce −R1 through −R6, respectively. As can be seen from FIG. 14, commutating signal 208 is created by adding ramp components −R1, +R2, +R3, −R4, −R5 and +R6. Accordingly, those outputs in FIG. 9 are connected to bus 286 through summing resistors 287 through 292. Amplifier 293 sums its inputs and provides commutating signal 208. Amplifier 294 inverts signal 208 to provide the inverse 207 of energizing signal 208 which can be used to produce negative torque on rotor assembly 64.

FIG. 10 shows the circuit used to construct commutating signal 210. Points A through F of the circuit shown in FIG. 10 are connected to the circuit shown in FIG. 9 at points A through F, respectively. The circuit shown in FIG. 10 operates identically to circuit 298 shown in FIG. 9, except that a different sequence of ramp functions is combined to produce commutating signal 210. In particular, circuit 295 combines ramps −R1, −R2, +R3, +R4, −R5 and −R6. Accordingly, bus 296 is electrically connected to those outputs. Inverter 297 inverts signal 210.

FIG. 15 shows the position circuit that creates the position signal 204. Position circuit 400 consists of two circuits 402 and 404. Circuit 402 is a carefully regulated crystal oscillator circuit that operates at 492 kHz. The output of circuit 402 is used to excite position sensing coils P1 and P2. Position sensing coils P1 and P2 are excited with a signal of a frequency substantially below the frequency of the ultrasound echoes returning to probe 10 to avoid production of any significant harmonics that could interfere with the processing of the echoes. Crystal 406 oscillates at 492 kHz and is connected to dual field effect transistor 408 of conventional Pierce oscillator circuit 410. Tuned tank 412 is connected to a center tap transformer 414, the secondary of which drives a differential buffer amplifier 416. The output of amplifier 416 is connected to phase inverter 418 which drives two diode pumps 420. The voltage at 422 is applied to differential amplifier 424 and compared to a reference voltage 426, which can be adjusted by potentiometer 428. The output of differential amplifier 424, an error correction signal, is applied to feedback line 430 through a suitable clamping circuit 432 to limit the range of the regulating action. Clamping circuit 432 protects field effect transistor 408. The signal on line 430 is applied to the shield gate of transistor 408 and causes transistor 408 to perform like an amplitude-regulated Pierce oscillator. Accordingly, circuit 402 provides amplitude control at exactly four volts peak-to-peak as measured from point 434 to ground and from point 436 to ground. A pure sine wave of four volts peak-to-peak is produced at points 434 and 436.

The signals at points 434 and 436 are applied to constant current transistors 438 and 440, respectively. Transistors 438 and 440 excite position sensing coils P1 and P2. Accordingly, as sensor strip 124 is moved by mirror assembly 72, the impedances on coils P1 and P2 change differentially and the envelopes of the 492 kHz signal varies sinusoidally at points 442 and 444. Amplifiers 446 and 448 are buffers that prevent detectors 450 and 452 from transmitting distortion back to coils P1 and P2 which otherwise could lead to interference appearing in the ultrasound image. Accordingly, the position signal can be detected without introducing harmonic distortion into coils P1 and P2. Similarly, amplifier 418 provides the same type of buffering for the regulator circuitry. The output of detectors 450 and 452 are complementary, the output of detector 450 being positive and the output of detector 452 being negative. Circuit 454 is a low-noise operational amplifier which amplifies and inverts the signal at 456. The output of each detector 450 and 452 applied differentially to point 456 and the signal on feedback path 458 is also applied to point 456 to sum those signals. The comparison of the outputs of detectors 450 and 452 appears at point 460 and constitutes position signal 204.

What is claimed is:

1. An ultrasound probe for examining an object comprising:
   means for emitting ultrasound energy;
   means for deflecting said emitted ultrasound energy;
   means for driving said deflecting means including:
   a stator assembly having at least two sets of electrically conductive coils, at least one said set being displaced from one other set;
   a magnet assembly mounted in confronting relationship to said stator assembly and being movable relative thereto, said magnet assembly having a plurality of magnetic poles, movement of said magnet assembly causing corresponding movement of said deflecting means;
   means for providing a position signal related to the position of said deflecting means relative to said stator assembly;
   means for processing said position signal to generate continuously varying commutating signals in a number corresponding to the number of said sets of coils;
   means for generating a command signal;
   means for comparing said position signal with said command signal and thereby generating a signal error;
   means for continuously applying said error signal to said commutating signals to alter at least one of their amplitude and polarity; and
   means for applying said altered commutating signals to their respective said sets of coils to move said magnet assembly in a uniform and continuous motion irrespective of the number of sets of coils and number of magnet poles.

2. The ultrasound probe recited in claim 1 wherein said deflecting means is an acoustical mirror.

3. The ultrasound probe of claim 1, wherein
   said means for deflecting reflects the returned ultrasound energy to said means for emitting; and
   said means for emitting receives the reflected returned ultrasound energy.

4. The ultrasound probe of claim 1, further comprising
   a sealed housing containing an ultrasound energy transmissible liquid, wherein at least one of said means for emitting and said means for deflecting is mounted within said sealed housing.

5. The ultrasound probe of claim 1, wherein
   said stator assembly comprises a thin flat stator.

6. The ultrasound probe of claim 1, wherein
   said magnet is a permanent magnet.

7. The ultrasound probe of claim 6, wherein
   said permanent magnet is a thin flat permanent magnet.

8. The ultrasound probe of claim 1, wherein
   said altered commutating signals are applied as current commands to their respective coils.

9. An ultrasound probe for examining an object comprising:
   a sealed housing that contains an ultrasound energy transmissible liquid;
   an ultrasound acoustical mirror stationarily mounted within said housing for emitting and receiving ultrasound energy and converting said ultrasound energy to electrical signals;
   an acoustical mirror assembly mounted within said housing for rotational movement for deflecting said emitted ultrasound energy and for deflecting returning ultrasound energy to said crystal;
   means for rotating said acoustical mirror assembly including:
   a thin flat stator assembly stationarily mounted relative to said housing and having two sets of electrically conductive coils, each said set having six windings, each said set being displaced from the remaining said set;
   a thin flat permanent magnet assembly mounted in confronting relationship to said stator assembly and being rotatably movable relative thereto, said magnet assembly having six poles, said crystal being mounted to said magnet assembly;

means for providing a position signal related to the angular position of said acoustical mirror relative to said stator assembly including:
a pair of position sensing coils disposed within said housing proximate a surface of said acoustical mirror assembly and energized by a source of high frequency electrical current; and
a position sensor strip secured to said surface of said acoustical mirror assembly that reduces the inductance of the voltage developed across a said position sensing coil when said strip is disposed within the magnetic field generated by said position sensing coil, said position sensing strip and said coils being so mounted within said housing that the sum of the voltages developed across said position sensing coils is substantially constant regardless of the position of said acoustical mirror assembly, said position signal being related to the difference between the voltages across said position sensing coils;
means for processing said position signal to generate two angularly periodic commutating signals which are shifted in angle from each other;
means for generating a periodically time-varying command signal;
means for comparing said position signal with said command signal and thereby generating an error signal;
means for applying said error signal to said commutating signal to alter at least one of their amplitude and polarity;
means for applying said altered commutating signals as current commands to their respective said sets of coils to cause movement of said acoustical mirror assembly to follow said command signal; and
means for causing said crystal to emit a timed series of ultrasound pulses at a predetermined frequency.

10. A system having infinite angular resolution for driving an object that is movable relative to the stator assembly of its driving motor comprising:
said stator assembly having at least two sets of electrically conductive coils, at least one said set being displaced from at least one other set;
a magnet assembly mounted in confronting relationship to said stator assembly and being movable relative thereto, said magnet assembly having a plurality of magnetic poles, movement of said magnet assembly causing corresponding movement of said object;
means for providing a position signal related to the position of said object relative to said stator assembly;
means for processing said position signal to generate continuously varying commutating signals in a number corresponding to the number of said sets of coils;
means for generating a command signal;
means for comparing said position signal with said command signal and thereby generating an error signal;
means for continuously applying said error signal to said commutating signals to alter at least one of their amplitude and polarity; and
means for applying said altered commutating signals to their respective said sets of coils to cause movement of said object to directly follow said command signal in a uniform and continuous motion irrespective of the number of sets of conductive coils and the number of magnetic poles.

11. A system for providing rotational movement to the ultrasound crystal assembly of an ultrasound probe comprising:
a thin flat stator assembly stationarily mounted relative to said housing and having two sets of electrically conductive coils, each said set having six windings, and being displaced from the remaining said set;
a thin flat permanent magnet assembly mounted in confronting relationship to said stator assembly and being rotatably movable relative thereto, said magnet assembly having six poles, said crystal being mounted to said magnet assembly;
means for providing a position signal related to the angular position of said crystal relative to said stator assembly including:
a pair of position sensing coils disposed within said housing proximate said crystal and energized by a source of high frequency electrical energy; and
means mounted to said crystal assembly proximate said position sensing coils for reducing the inductance and the voltage developed across a said position sensing coil when said reducing means is disposed within the magnetic field generated by said position sensing coil, said reducing means and said coils being so mounted within said housing that the sum of the voltages developed across said position sensing coils are substantially constant regardless of the position of said reducing means, said position signal being related to the difference between the voltages across said position sensing coils;
means for processing said position signal to generate two angularly periodic commutating signals which are shifted in angle from each other;
means for generating a periodically time-varying command signal;
means for comparing said position signal with said command signal and thereby generating a error signal;
means for applying said error signal to said commutating signals to alter at least one of their amplitude and polarity; and
means for applying said altered commutating signals as current commands to their respective said sets of coils to cause movement of said crystal assembly to follow said command signal.

12. An ultrasound probe for examining an object comprising:
an ultrasound transducer for emitting ultrasound energy;
means for deflecting said emitted ultrasound energy including:
a stator assembly having a plurality of sets of electrically conductive coils, each said set being displaced from the remaining said sets;
means for providing a position signal related to the angular position of said means for deflecting relative to said stator assembly including:
a pair of position sensing coils energized by a source of high frequency electrical current; and
a position sensor strip secured to said surface of said means for rotational movement proximate said position sensing coils, wherein said strip reduces the magnitude of the voltage developed across a said position sensing coil and provides a corresponding increase in magnitude of voltage across the remaining position sensing coil according to the position of said strip in he magnetic field generated by said position sensing coil, said position sensing strip and said coils being so mounted within said housing that the sum of the voltages developed across said position sensing coils is substantially constant regardless of the position of said means for rotational movement, said position signal being related to the difference between the voltages across said position sensing coils;

means for processing said position signal to generate two angularly periodic commutating signals which are shifted in angle from each other;

means for generating a command signal;

means for comparing said position signal with said command signal and thereby generating an error signal;

means for applying said error signal to said commutating signal to alter at least one of their amplitude and polarity;

means for applying said altered commutating signals to their respective said coils to cause movement of said means for rotational movement to follow said command signal.

13. The ultrasound probe of claim 12, wherein said ultrasound transducer is a crystal element.

14. The ultrasound probe of claim 12, further including a housing assembly wherein said ultrasound transducer is stationarily mounted to said housing.

15. The ultrasound probe of claim 12, wherein said means for rotational movement comprises an acoustical mirror.

16. The ultrasound probe of claim 12, wherein said set of stator coils includes a plurality of windings.

17. The ultrasound probe of claim 16, wherein said stator includes two sets of coils, each set including six windings.

18. The ultrasound probe of claim 12, further including
a magnet assembly mounted in confronting relationship relative thereto, said magnet assembly having a plurality of poles, movement of said magnet assembly causing corresponding movement of said means for rotational movement.

19. The ultrasound probe of claim 18 wherein said magnet assembly includes a permanent magnet.

20. The ultrasound probe of claim 12, wherein said command signal is periodically varying.

* * * * *

UNITED STATES PATENT AND TRADEMARK OFFICE
CERTIFICATE OF CORRECTION

PATENT NO. : 4,479,388
DATED : October 30, 1984
INVENTOR(S) : Terrance Matzuk

It is certified that error appears in the above—identified patent and that said Letters Patent is hereby corrected as shown below:

| | | |
|---|---|---|
| Column 1 | Line 62, | "preferrable" should read --preferable-- |
| Column 4 | Line 51, | "a opening" should read --an opening-- |
| Column 5 | Line 61, | "passes though" should read --passes through-- |
| Column 6 | Line 31, | "a teflon rod that slips" should read --a rod constructed of such a synthetic fluorine-containing resin as that sold under, the trademark TEFLON. The rod slips-- |
| | Line 32, | "into a teflon tube" should read --into a tube-- |
| | Line 32, | "material as is" should read --material as-- |
| Column 7 | Lines 4 & 5 | "one return lead - are" should read --one return lead- are-- |
| Column 8 | Line 41, | "incident beam" should read --incident beams-- |
| Column 9 | Line 27, | "drives 220 and 222" should read --drivers 220 and 222" |
| | Lines 32 & 33 | "adjacent windings - Al" should read --adjacent windings - Al-- |
| | Line 35, | "208, and 210." should read --208 and 210.-- |

UNITED STATES PATENT AND TRADEMARK OFFICE
CERTIFICATE OF CORRECTION

PATENT NO. : 4,479,388

DATED : October 30, 1984

INVENTOR(S) : Terrance Matzuk

It is certified that error appears in the above—identified patent and that said Letters Patent is hereby corrected as shown below:

Column 12 Line 49, "an ultrasound acoustical mirror stationarily" should read --an ultrasound crystal stationarily--

Lines 67 & 68 "said crystal being" should read --said acoustical mirror being--

Column 14 Line 41, "a error" should read --an error--

Column 15 Line 3, "in he mag-" should read --in the mag- --

Signed and Sealed this

Thirty-first Day of December 1985

[SEAL]

Attest:

DONALD J. QUIGG

Attesting Officer

Commissioner of Patents and Trademarks